United States Patent
Price et al.

(10) Patent No.: US 9,657,391 B2
(45) Date of Patent: May 23, 2017

(54) OPTICAL TRANSMISSION/REFLECTION MODE IN-SITU DEPOSITION RATE CONTROL FOR ICE FABRICATION

(71) Applicant: Halliburton Energy Services, Inc., Houston, TX (US)

(72) Inventors: James M. Price, The Woodlands, TX (US); Aditya B. Nayak, Humble, TX (US); David L. Perkins, The Woodlands, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 125 days.

(21) Appl. No.: 14/432,844

(22) PCT Filed: May 8, 2014

(86) PCT No.: PCT/US2014/037277
§ 371 (c)(1),
(2) Date: Apr. 1, 2015

(87) PCT Pub. No.: WO2015/171149
PCT Pub. Date: Nov. 12, 2015

(65) Prior Publication Data
US 2016/0130696 A1    May 12, 2016

(51) Int. Cl.
*G01B 11/28* (2006.01)
*C23C 14/54* (2006.01)
(Continued)

(52) U.S. Cl.
CPC .............. *C23C 14/54* (2013.01); *C23C 14/22* (2013.01); *C23C 14/30* (2013.01); *C23C 14/545* (2013.01);
(Continued)

(58) Field of Classification Search
CPC  G01N 21/21; G01N 21/41; G01J 4/00; C23C 14/0042; C23C 14/54; C23C 14/30;
(Continued)

(56) References Cited

U.S. PATENT DOCUMENTS 5,028,136 A * 7/1991 Murarka ................. C03C 17/22
356/485
6,113,733 A * 9/2000 Eriguchi ............. H01L 21/3065
156/345.24

(Continued)

FOREIGN PATENT DOCUMENTS

EP       2508645 A1    10/2012
JP    2005002462 A     1/2005
(Continued)

OTHER PUBLICATIONS

International Search Report and Written Opinion for PCT/US2014/037277 dated Feb. 25, 2015.

*Primary Examiner* — Tarifur Chowdhury
*Assistant Examiner* — Isiaka Akanbi
(74) *Attorney, Agent, or Firm* — McDermott Will & Emery LLP

(57) ABSTRACT

Systems and methods of controlling a deposition rate during thin-film fabrication are provided. A system as provided may include a chamber, a material source contained within the chamber, an electrical component to activate the material source, a substrate holder to support the multilayer stack and at least one witness sample. The system may further include a measurement device and a computational unit. The material source provides a layer of material to the multilayer stack and to the witness sample at a deposition rate controlled at least partially by the electrical component and based on a correction value obtained in real-time by the computational unit. In some embodiments, the correction value is based on a measured value provided by the mea- (Continued)

surement device and a computed value provided by the computational unit according to a model.

23 Claims, 6 Drawing Sheets

(51) Int. Cl.
| | |
|---|---|
| *C23C 14/30* | (2006.01) |
| *G01B 11/06* | (2006.01) |
| *G01N 21/41* | (2006.01) |
| *G02B 1/12* | (2006.01) |
| *G02B 5/28* | (2006.01) |
| *C23C 14/22* | (2006.01) |

(52) U.S. Cl.
CPC ............ *G01B 11/06* (2013.01); *G01N 21/41* (2013.01); *G02B 1/12* (2013.01); *G02B 5/285* (2013.01)

(58) Field of Classification Search
CPC ......... C23C 14/545; G01B 11/06; G02B 1/12; G02B 5/285
USPC .......................... 356/630, 337, 369, 326, 632
See application file for complete search history.

(56) References Cited

U.S. PATENT DOCUMENTS

| | | | | |
|---|---|---|---|---|
| 6,636,309 | B1* | 10/2003 | Johs | G01J 4/00 356/365 |
| 6,781,692 | B1* | 8/2004 | Rosencwaig | G01N 21/211 250/255 |
| 7,901,870 | B1* | 3/2011 | Wach | G02B 5/285 430/321 |
| 2005/0139966 | A1* | 6/2005 | Scarlete | C23C 16/325 257/632 |
| 2011/0119020 | A1* | 5/2011 | Key | G01J 5/00 702/135 |

FOREIGN PATENT DOCUMENTS

| | | |
|---|---|---|
| JP | 2005154804 A | 6/2005 |
| KR | 1020110090121 | 8/2011 |
| WO | 2015171149 A1 | 11/2015 |

* cited by examiner

OPTICAL TRANSMISSION/REFLECTION MODE IN-SITU DEPOSITION RATE CONTROL FOR ICE FABRICATION

This application is a National Stage entry of and claims priority to International Application No. PCT/US2014/037277, filed on May 8, 2014.

BACKGROUND

The present disclosure relates to optical thin-film fabrication and, more particularly, to systems and methods of controlling a deposition rate during optical thin-film fabrication.

In the field of thin-film device fabrication for optical purposes, the design of a multilayered thin-film device targets a specific spectral performance. As each of the layers is formed in a stack, fabrication variability results in a multilayered film that may have inconsistent values of the optical properties of different layers made of the same material. Inconsistencies may arise, for example, from manufacturing variability associated with temperature and pressure control inside a deposition chamber. Once fabrication of the thin-film device is finished and tested, fabrication errors in the thin-film device that are beyond a specified tolerance result in the thin-film device being discarded and fabrication of a new thin-film device is then required. As can be appreciated, this procedure results in waste of time and materials, in detriment of fabrication cost efficiency.

Current fabrication techniques provide real-time monitoring of layer thickness using changes in the mechanical properties of a quartz crystal as a layer is deposited on its surface. However, these techniques fail to provide optical properties relevant to the functionality of the optical thin-film. Furthermore, measurement of mechanical properties of a quartz crystal can be noisy, and thereby result in reduced accuracy.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

Figure 1:
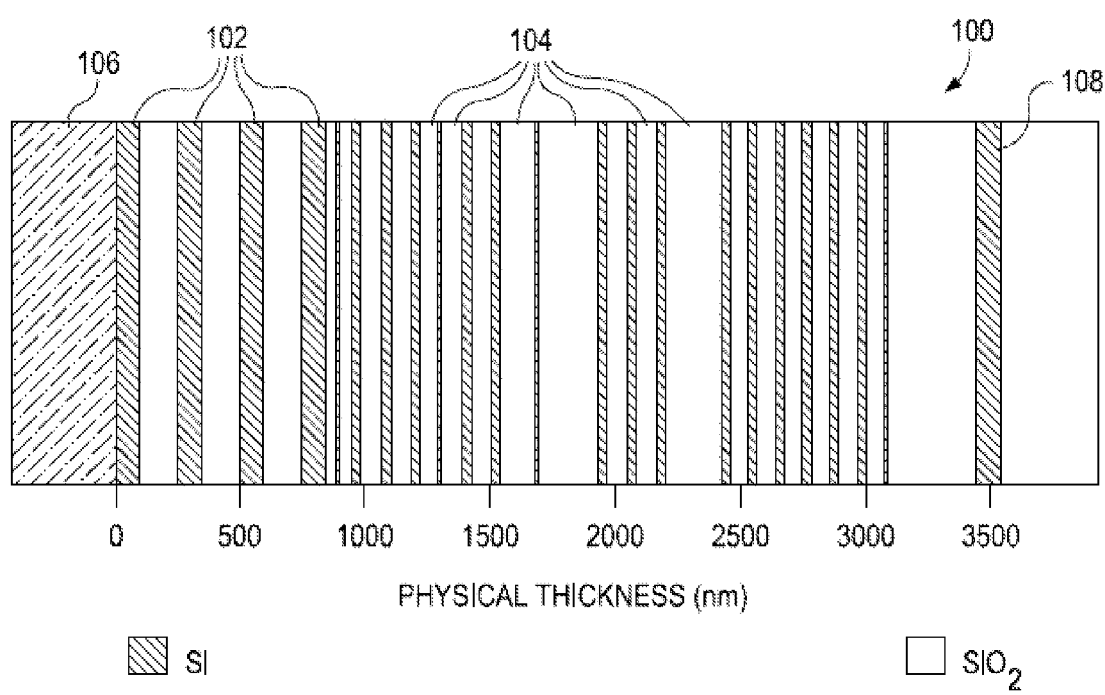
FIG. 1 illustrates an exemplary integrated computational element (ICE), according to some embodiments.

The present disclosure relates to optical thin-films and, more particularly, to systems and methods of using optical methods for measuring and controlling deposition rates in the fabrication of optical thin-films.

Systems and methods of controlling a deposition rate during optical thin-film fabrication are provided. A system consistent with embodiments herein may include a chamber, a material source contained within the chamber, an electrical component to activate the material source, a substrate holder to prevent the substrate from moving during the deposition process and at least one witness sample. The system may further include a measurement device and a computational unit. The material source provides a layer of material to the multilayer stack, and to the witness sample at a deposition rate controlled at least partially by the electrical component and based on a correction value obtained by the computational unit. In some embodiments, the correction value is based on a measured value provided by the measurement device and a computed value provided by the computational unit according to a model.

Optical computing devices, also commonly referred to as "opticoanalytical devices," can be used to analyze and monitor a substance in real time. Such optical computing devices will often employ a light source emitting electromagnetic radiation that reflects or refracts from a substance and optically interacts with an optical processing element to determine quantitative and/or qualitative values of one or more physical or chemical properties of the substance. The optical element may be, for example, an integrated computational element (ICE), which may act as an optical interference based device that can be designed to operate over a continuum of wavelengths in the electromagnetic spectrum from the UV to mid-infrared (MIR) ranges, or any sub-set of that region. The ICE modifies and processes the electromagnetic radiation that optically interacts with the substance. A detector reads the modified interacted electromagnetic radiation, thus correlating an output of the detector to the physical or chemical property of the substance under analysis.

An exemplary optical thin-film based ICE typically includes a plurality of optical layers consisting of various materials whose index of refraction and size (e.g., thickness) may vary between each layer. The design of an ICE (referred to herein as an "ICE design") refers to the number and thicknesses of the respective layers of the ICE. The layers may be strategically deposited and sized so as to selectively pass predetermined fractions of electromagnetic radiation at different wavelengths configured to substantially mimic a regression vector corresponding to a particular physical or chemical property of interest of a substance. Accordingly, an ICE design will exhibit a transmission function that is weighted with respect to wavelength. As a result, the output light from the ICE conveyed to the detector may be related to the physical or chemical property of interest for the substance.

The present disclosure provides improved systems and methods for characterizing the deposition rates and optical properties of layers of material in optical thin-films, such as layers of an integrated computational element (ICE) during fabrication. The disclosed systems and methods may be suitable for the design and fabrication of ICEs. However, it will be appreciated that the various disclosed systems and methods are equally applicable to fabrication of any thin-film used in thin-film applications. Such application areas and technology fields may include, but are not limited to, the oil and gas industry, food and drug industry, industrial applications, the mining industry, the optics industry, the eyewear industry, the electronics industry, and the semiconductor fabrication industry.

As used herein, the term "characteristic" refers to a chemical, mechanical, or physical property of a substance. The characteristic of a substance may include a quantitative or qualitative value of one or more chemical constituents or compounds present therein or any physical property associated therewith. Such chemical constituents and compounds may be referred to herein as "analytes." Illustrative characteristics of a substance that can be detected with the ICEs described herein can include, for example, chemical composition (e.g., identity and concentration in total or of individual components), phase presence (e.g., gas, oil, water, etc.), impurity content, pH, alkalinity, viscosity, density, ionic strength, total dissolved solids, salt content (e.g., salinity), porosity, opacity, bacteria content, total hardness, transmittance, combinations thereof, state of matter (solid, liquid, gas, emulsion, mixtures, etc.), and the like.

As used herein, the term "substance," or variations thereof, refers to at least a portion of matter or material of interest to be tested or otherwise evaluated using the ICEs described herein. The substance includes the characteristic of interest, as defined above. The substance may be any fluid capable of flowing, including particulate solids, liquids, gases (e.g., air, nitrogen, carbon dioxide, argon, helium, methane, ethane, butane, and other hydrocarbon gases, hydrogen sulfide, and combinations thereof), slurries, emulsions, powders, muds, glasses, mixtures, combinations thereof, and may include, but is not limited to, aqueous fluids (e.g., water, brines, etc.), non-aqueous fluids (e.g., organic compounds, hydrocarbons, oil, a refined component of oil, petrochemical products, and the like), acids, surfactants, biocides, bleaches, corrosion inhibitors, foamers and foaming agents, breakers, scavengers, stabilizers, clarifiers, detergents, a treatment fluid, fracturing fluid, a formation fluid, or any oilfield fluid, chemical, or substance as found in the oil and gas industry. The substance may also refer to a solid material such as, but not limited to, rock formations, concrete, solid wellbore surfaces, and solid surfaces of any wellbore tool or projectile (e.g., balls, darts, plugs, etc.).

As used herein, the term "electromagnetic radiation" refers to radio waves, microwave radiation, terahertz, near/mid/deep infrared radiation, visible light, ultraviolet light, X-ray radiation and gamma ray radiation.

As used herein, the term "optically interact" or variations thereof refers to the reflection, transmission, scattering, diffraction, or absorption of electromagnetic radiation either on, through, or from one or more processing elements (i.e., an ICE or other ICE not characterized as an optical thin-film based device), a substance being analyzed by the processing elements, or a polarizer. Accordingly, optically interacted light refers to electromagnetic radiation that has been reflected, transmitted, scattered, diffracted, or absorbed by, emitted, or re-radiated, for example, using a processing element, but may also apply to optical interaction with a substance or a polarizer. In operation, an ICE is capable of distinguishing electromagnetic radiation related to a characteristic of interest of a substance from electromagnetic radiation related to other components of the substance.

Referring to FIG. 1, illustrated is an exemplary ICE 100, according to one or more embodiments of the present disclosure. As illustrated, the ICE 100 may include a plurality of alternating layers 102 and 104, such as silicon (Si) and $SiO_2$ (quartz), respectively. In general, these layers 102, 104 consist of materials whose real part of the index of refraction is high and low, respectively. More generally, the index of refraction is a complex number having an imaginary part associated with absorption effects. Other examples of materials might include niobia and niobium, germanium and germania, $MgF_2$, $SiO_2$, and other high and low index materials known in the art. Layers 102, 104 may be strategically deposited on an optical substrate 106. In some embodiments, optical substrate 106 is BK-7 optical glass. In other embodiments, optical substrate 106 may be another type of optical substrate, such as quartz, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like.

At the opposite end (e.g., opposite optical substrate 106 in FIG. 1), ICE 100 may include a layer 108 that is generally exposed to the environment of the device or installation, and may be able to detect a sample substance. The number of layers 102, 104 and the thickness of each layer 102, 104 are determined from the spectral attributes acquired from a spectroscopic analysis of a characteristic of the substance being analyzed using a conventional spectroscopic instrument. The spectrum of interest of a given characteristic typically includes any number of different wavelengths.

It should be understood that ICE 100 in FIG. 1 does not in fact represent any particular ICE configured to detect a specific characteristic of a given substance, but is provided for purposes of illustration only. Consequently, the number of layers 102, 104 and their relative thicknesses, as shown in FIG. 1, bear no correlation to any particular substance or characteristic thereof. Nor are layers 102, 104 and their relative thicknesses necessarily drawn to scale, and therefore should not be considered limiting of the present disclosure.

In some embodiments, the material of each layer 102, 104 can be doped or two or more materials can be combined in a manner to achieve the desired optical characteristic. In addition to solids, the exemplary ICE 100 may also contain liquids and/or gases, optionally in combination with solids, in order to produce a desired optical characteristic. In the case of gases and liquids, the ICE 100 can contain a corresponding vessel (not shown), which houses the gases or liquids. Exemplary variations of the ICE 100 may also include holographic optical elements, gratings, piezoelectric, light pipe, and/or acousto-optic elements, for example, that can create transmission, reflection, and/or absorptive properties of interest.

The multiple layers 102, 104 may exhibit different refractive indices. By properly selecting the materials of layers 102, 104 and their relative thickness and spacing, ICE 100 may be configured to selectively pass/reflect/refract predetermined fractions of electromagnetic radiation at different wavelengths. Each wavelength is given a predetermined weighting or loading factor. The thickness and spacing of the layers 102, 104 may be determined using a variety of approximation methods from the spectrum of the characteristic or analyte of interest. These methods may include inverse Fourier transform (IFT) of the optical transmission spectrum and structuring the ICE 100 as the physical representation of the IFT. The approximations convert the IFT into a structure based on known materials with constant refractive indices.

The weightings that layers 102, 104 of ICE 100 apply at each wavelength may be set to the regression weightings described with respect to a known equation, data, or spectral signature. For instance, when electromagnetic radiation interacts with a substance, unique physical and chemical information about the substance may be encoded in the electromagnetic radiation that is reflected from, transmitted through, or radiated from the substance. This information is often referred to as the spectral "fingerprint" of the substance. ICE 100 may be configured to perform the dot product of the received electromagnetic radiation and the wavelength dependent transmission function of the ICE 100. The wavelength dependent transmission function of ICE 100 is dependent on the material refractive index of each layer, the number of layers 102, 104 and thickness of each layer 102, 104. Thus, it can be appreciated that performing spectroscopic measurements on layers 102, 104 during fabrication may indicate proper or improper refractive indices and layer 102, 104 thicknesses, and further enable correction adjustments as necessary for proper operation of ICE 100 upon fabrication completion.

Embodiments consistent with this disclosure provide a thin-film based optical measurement approach to control the deposition rate of a layer. The thin-film based optical measurement may be applied during fabrication of an optical thin-film. The thin-film stack, for example, may be an ICE as described herein. The precise stoichiometry of a deposited layer has an impact on the optical properties of thin-films. The stoichiometry may be controlled during the fabrication process by establishing and otherwise regulating the deposition rate of the layer. A reliable, constant, or approximately constant deposition rate (during thin-film deposition) may enable both the high index of refraction (the real part) (e.g., Si) and low index of refraction (the real part) (e.g., $SiO_2$) layers to maintain a consistent specification during the course of the ICE fabrication process. Moreover, a more precise control of the deposition rate enhances the accuracy of end-point detection for layer termination, thus enabling precise layer thickness results in the fabrication process. Thus, embodiments consistent with the present disclosure may avoid overshoot errors resulting in layers having a thickness greater than desired. It will be appreciated by those skilled in the art that embodiments in this disclosure may be used in combination with alternative deposition rate detection methods such as a quartz crystal monitoring system.

Figure 2:
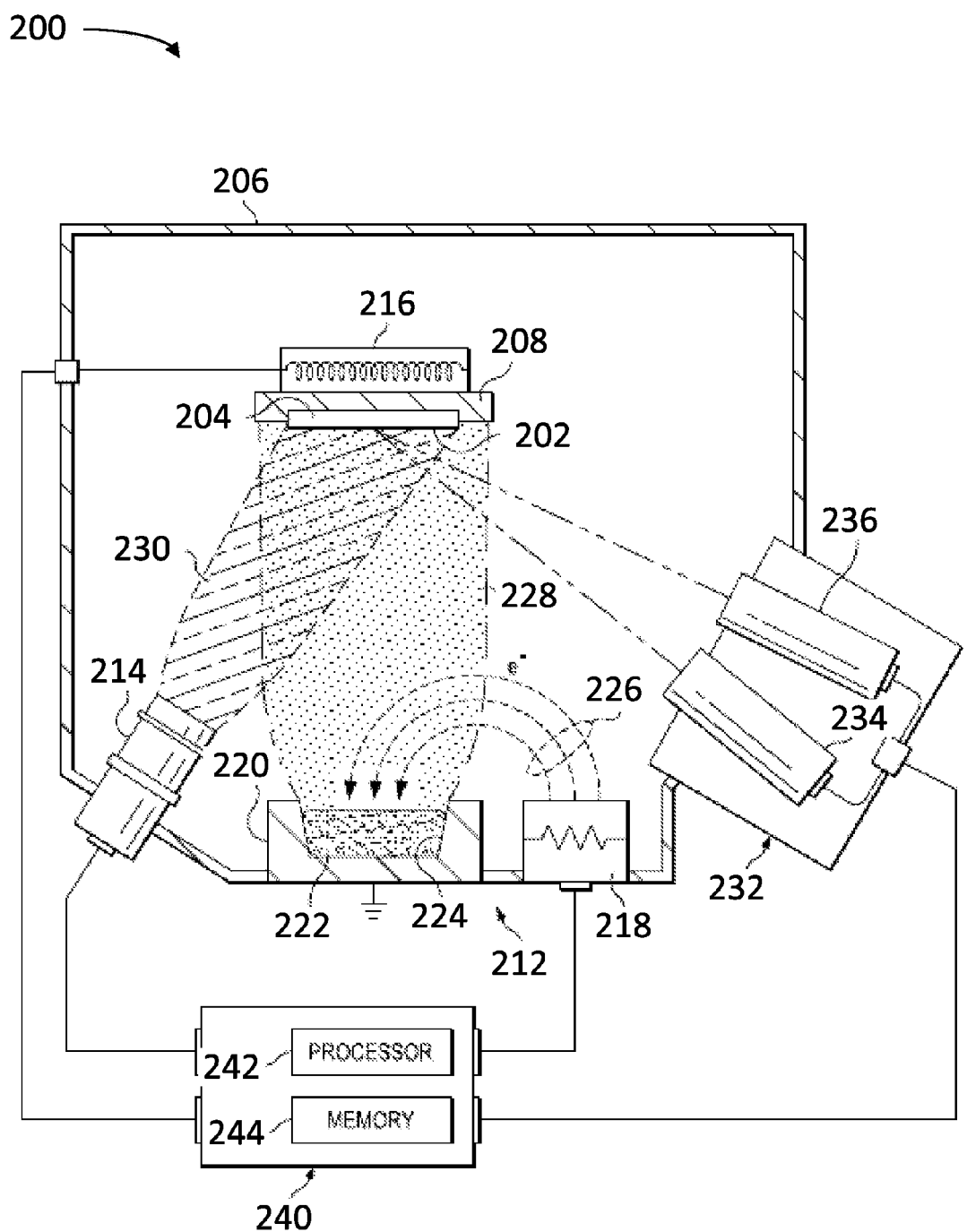
FIG. 2 illustrates an exemplary system for fabricating a thin-film device, according to some embodiments.

FIG. 2 illustrates an exemplary system 200 that may be used for fabricating a thin-film device, according to one or more embodiments. Accordingly, system 200 may be configured to fabricate an ICE 202 on a substrate 204. The substrate 204 may be similar to and made of one or more of the previously mentioned materials for the optical substrate 106 of FIG. 1, and therefore will not be described again. In some embodiments, ICE 202 is configured to transmit an optical spectrum representing a chemical constituent of a production fluid from a wellbore or other fluid. According to some embodiments, ICE 202 may be configured to reflect an optical spectrum representing a chemical constituent of a production fluid from a wellbore or other fluid.

System 200 includes a chamber 206, or vessel, and a substrate holder 208. In some embodiments, chamber 206 may be placed and maintained at a low pressure to facilitate material deposition. Accordingly, in some embodiments chamber 206 may be set to about $10^{-7}$ Torr. Substrate holder 208 secures substrate 204 within chamber 206 relative to a mass-flux generator 212 and an ion-beam generator 214. Substrate holder 208 may include a heater 216 for raising and maintaining a temperature of substrate 204 above ambient. In some embodiments, heater 216 may be mechanically decoupled from substrate 204. For example, in one embodiment, heating lamps, (e.g., halogen lamps) inside chamber 206 may be used to uniformly heat the entire chamber 206 and substrate 204 to a desired temperature.

Mass-flux generator 212 is coupled to chamber 206 and may include an electron gun 218 and a crucible 220 for heating a mass source 222. Mass source 222 is contained within a pocket 224 of the crucible 220 and sits adjacent the electron gun 218. The electron gun 218 is configured to generate a beam of electrons 226 from a filament and arc the beam of electrons 226 into the pocket 224 of the crucible 220 via an electromagnetic field. The electromagnetic field used to direct electron beam 226 onto mass source 222 may be generated with a magnetron, according to some embodiments. Energy from electron beam 226 is absorbed by mass source 222, inducing evaporation of the mass source. A water cooling circuit (not shown) may also be incorporated into the crucible 220 to prevent the crucible 220 from decomposing or melting. Crucible 220 is electrically grounded, and evaporation of mass source 222 is operable to generate a mass flux 228 that may be received by substrate holder 208.

Mass flux 228 may include elements, molecules, or a combination thereof. Impingement of the mass flux 228 onto the substrate 204, or onto existing films already formed on the substrate 204, forms a film in ICE 202. In some embodiments, crucible 220 may include two or more pockets 224 for holding two or more different mass sources 222. In such embodiments, electron gun 218 arcs the beam of electrons 226 into the appropriate pocket 224 to heat the desired mass source 222. This configuration may allow system 200 to fabricate ICE 202 with minimal exposure of chamber 206 to an ambient environment (i.e., to introduce a new or different mass source 222). In at least one embodiment, crucible 220 contains two or more pockets 224 for containing mass sources of Si and $SiO_2$. In these embodiments, mass-flux generator 212 is operational to form films of, respectively; Si and $SiO_2$ (e.g., ICE 100 in FIG. 1). It should be understood that other techniques may be used; for example, without limitation, two separate electron guns for Si and $SiO_2$, respectively, might equally be used, without departing from the scope of the disclosure.

Ion-beam generator 214 may be configured to produce and direct an ion beam 230 of elements, molecules, or a combination thereof towards substrate 204. Ion beam 230 impinges upon the forming film and may promote control over film properties such as morphology, density, stress level, crystallinity, and chemical composition. In some embodiments, ion-beam generator 214 may produce ion beam 230 using a mixed gas source. The mixed gas source may be pre-mixed before introduction into the chamber 206 or may be mixed in chamber 206, proximate to ion-beam generator 214. Non-limiting examples of mixed gas sources include argon gas and silane gas; argon gas and methane gas; and argon gas, methane gas, and tetrafluoromethane gas. The aforementioned mixed gas sources are operable to form films of, respectively, hydrogenated amorphous silicon films, films of silicon carbide, and films of silicon carbide alloy, $Si_{1-x-y-z}C_xH_yF_z$. The compositional boundaries of the silicon carbide alloy are defined by the relation: $x+y+z<1$ where x is non-zero.

Accordingly, in some embodiments system 200 may encompass an Ion Assisted E-beam deposition tool in which the rate of evaporation in crucible 220 is proportional to the voltage applied to the E-beam by electron gun 218. A higher voltage increases the evaporation and deposition rate onto ICE 202, resulting in a less dense layer. Conversely, lowering the voltage in electron gun 218 decreases deposition rate and produces a denser layer. More generally, deposition rate during E-beam evaporation and other physical vapor deposition methods may be affected by factors other than a voltage in electron gun 218. A change in deposition rate can result from numerous dynamic process variables such as pressure, pumping speed, and temperature in chamber 206. Other factors that may affect the deposition rate include, but are not limited to, the source material surface and preparation, cooling of electron gun 218 and of crucible 220, and flux of ion beam generator 214.

Some of the above mentioned dynamic process variables fluctuate during the fabrication process. In many instances, these fluctuations become difficult to monitor and control as would be desirable. Some embodiments overcome the variability in thin-film deposition rate by monitoring the deposition rate (in real time) and providing the data to a proportional-integral-derivative (PID) loop which then adjusts the voltage of electron gun 218.

In some embodiments, as illustrated, a measurement device 232 may be coupled to or otherwise associated with chamber 206. Measurement device 232 is oriented towards substrate 204 and configured to measure in-situ a thickness, a complex index of refraction, or both, of a film being formed by mass-flux generator 212. Accordingly, measurement device 232 may be configured to perform optical, mechanical, and even electrical measurements on ICE 202. In some embodiments, measurement device 232 includes an ellipsometer 234 for measuring the thickness, the complex index of refraction, or both. In some embodiments, measurement device 232 includes a spectrometer 236 for measuring an optical spectrum of ICE 202 during fabrication. In some embodiments, measurement device 232 includes a quartz monitor or a single wavelength monitor for thickness. The quartz monitor includes the use of a quartz crystal microbalance as the deposition rate monitor. During deposition, the quartz crystal monitor measures the deposition rate and feeds the results into a proportional-integral-derivative (PID) loop to correct voltage in electron gun 218. Some embodiments may include a plurality of quartz crystal microbalances arranged in different points within chamber 206. Thus, averaging the measurements of the multiple crystal monitors placed inside chamber 206 may provide accurate deposition rate values.

Measurement device 232 may include an optical monitor such as an ellipsometer 234, and a spectrometer 236. More specifically, measurement device 232 may include a broadband light source and a CCD array detector. In some configurations, measurement device 232 collects optical data from a witness sample in real time. The optical data is incorporated into an optical model to determine film thickness (as a function of time). The calculated deposition rate is then forwarded to the PID loop to correct the voltage of electron gun 218. More specifically, the optical data may include a transmission spectrum, a reflection spectrum, an interference spectrum, or a combination thereof. The optical model then matches the measured optical data (e.g., spectra) with a selected layer thickness. Accordingly, in some embodiments the selected layer thickness is determined from the optical model that best fits the data.

Optical measurements may also prove useful in obtaining further information from the thin-film deposition process in addition to the thickness of the layer. For instance, optical measurements may provide the real and imaginary components of the complex index of refraction, n and k, of a layer, in real time. In that regard, when the optical properties of the layers change during fabrication, this information can be relayed back to electron gun 218, to correct for it. For example, second, third, fourth and further Si layers desirably have similar indices of refraction, regardless of their different thicknesses. However, a lower index of refraction may indicate a more porous film, fabricated at a higher deposition rate. If during the course of Si deposition, the measured index of refraction is lower than a predetermined standard value, this information can be relayed to the PID loop in order to alter operation of electron gun 218 and thereby decrease E-beam voltage to reduce deposition rate and yield a more dense Si material.

In embodiments consistent with the present disclosure, the PID loop may prove useful in helping to continuously adjust and otherwise maintain a voltage in electron gun 218 and other parameters, such as pressure and temperature inside chamber 206, thereby inducing a desired deposition rate. Further, according to some embodiments, the PID loop may also be configured to help control the electromagnetic field used to generate electron beam 226. Deposition rates in system 200 may vary from about 1 to about 5 Angstrom per second (Å/sec). In embodiments consistent with the present disclosure, the deposition rate may be controlled to within a fraction of an Å/sec.

For example, in some embodiments consistent with the present disclosure, a deposition rate of about 3 Å/sec may be controlled by a PID loop to within approximately 0.25 Å/sec or even less. In that regard, optical measurements obtained as disclosed herein may provide a more accurate and less noisy value for the deposition rate relative to the quartz crystal microbalance measurements. Accordingly, optical measurements obtained as disclosed herein include thin-film models that use optical parameters across a broad spectral band, therefore providing a more robust measurement for the layer thickness. As can be appreciated, a more robust optical measurement may be less prone to drift or adversely affected by system fluctuations.

While not explicitly shown, in some embodiments, measurement device 232 may include a probe and a detector disposed on opposing sides of chamber 206 and at the same angle of incidence. While probes, e.g., ellipsometer 234 and spectrometer 236, may be coupled on one side of the chamber 206, it should be understood that corresponding detectors may be coupled on an opposite side of the chamber 206. Accordingly, FIG. 2 depicts measurement device 232, in 'reflection mode.' In other embodiments, however, measurement device 232 may be configured in transmission mode. Substrate 204 in FIG. 2 may act as a 'witness sample,' according to some embodiments. A witness sample, for example, may be a substrate that may include ICE 202 or a test film, on which measurement device 232 performs optical measurements.

A computational unit 240 may be communicably coupled to mass-flux generator 212 and to ion-beam generator 214. Computational unit 240 may include one or more processors 242 and one or more memories 244 to control film formation during fabrication of the ICE 202. Computational unit 240 may be further coupled to the heater 216, if present, to manipulate the temperature of the substrate 204 during fabrication. Computational unit 240 couples measurement device 232 to control the thickness, the complex index of refraction, or both, of a layer formed by mass-flux generator 212. Accordingly, in some embodiments, computational unit 240 may execute the PID loop.

In exemplary operation of the system 200, a vacuum is formed in chamber 206 and an electron beam 226 emanates from the electron gun 218. Electron beam 226 is directed into pocket 224 of crucible 220 by the electromagnetic field. Evaporation of mass source 222 produces mass flux 228, which traverses a distance from the crucible 220 to substrate holder 208. Mass-flux generator 212 directs mass-flux 228 toward substrate 204 to form a layer in ICE 202. The layers in ICE 202 may include a dielectric layer (such as $SiO_2$), or a semiconducting layer (such as Si), or even a conducting layer (such as Aluminum —Al—).

In coordination with mass-flux generator 212, ion-beam generator 214 directs ion beam 230 towards substrate 204. Such coordination may be managed by computational unit 240 to control film formation during fabrication of the integrated computational element 202. When a layer has achieved its desired thickness, computational unit 240 deactivates mass-flux generator 212 and ion beam generator 214. Heater 216, if present, may be functional during the formation process in order to improve film properties. Computational unit 240 regulates mass-flux generator 212 and ion beam generator 214 to form a series of sequential films. The number, thickness, and refractive index (i.e., material) of sequential films in the series may be specified by a target transmission or reflection spectrum of ICE 202. Similar to the construction of the ICE 100 of FIG. 1, the design of ICE 202 produces alternating layers 102 (FIG. 1) of high index of refraction and layers 104 (FIG. 1) of low index of refraction. A terminal or capping layer 108 (FIG. 1) may also be formed.

During fabrication of ICE 202, computational unit 240 also controls measurement device 232. Measurement device 232 is operational to measure in-situ a thickness, a complex index of refraction, or both, of a layer formed in ICE 202. Measurement device 232 may be configured to perform an optical measurement on ICE 202, for example, for at least one wavelength. In some embodiments, measurement device 232 may include a broadband system to measure reflection/transmission spectra at multiple wavelengths. For example, in some embodiments a broadband reflection/transmission measurement may span a continuous multi-wavelength wavelength range from about 1.4 µm to about 2.5 µm, or more.

The optical measurement on ICE 202 may be in transmission mode, in reflection mode, or in transmission and reflection modes. In some embodiments, computational unit 240 stores the optical measurement in a database, as each of the layers is deposited on ICE 202. In some embodiments, computational unit 240 may also incorporate the optical measurement into the PID loop to adjust the deposition rate in real time, if desired. One or more processors 242 and one or more memories 244 of computational unit 240 are operable to develop or receive an optical model of ICE 202 as is being fabricated, using data stored in the database. Processors 242 and memories 244 may use the optical model to obtain a thickness of the layer deposited on ICE 202, in combination with data provided by measurement device 232.

Consistent with the present disclosure, ICE 202 may be fabricated using systems that employ other deposition techniques. Deposition techniques used to form the layers in ICE 202 may include, but are not limited to, unassisted electron beam evaporation, thermal evaporation, dc-sputtering, dc-magnetron sputtering, rf-sputtering, reactive physical vapor deposition (RPVD), physical vapor deposition (PVD), pulsed laser deposition (PLD), low pressure chemical vapor deposition (LPCVD), plasma-enhanced chemical vapor deposition (PECVD), atmospheric pressure chemical vapor deposition (APCVD), metal organic chemical deposition (MOCVD), and molecular beam epitaxy (MBE). Other deposition techniques are possible, by any feasible combination of the above techniques, as one of ordinary skill will recognize.

Figure 3A:
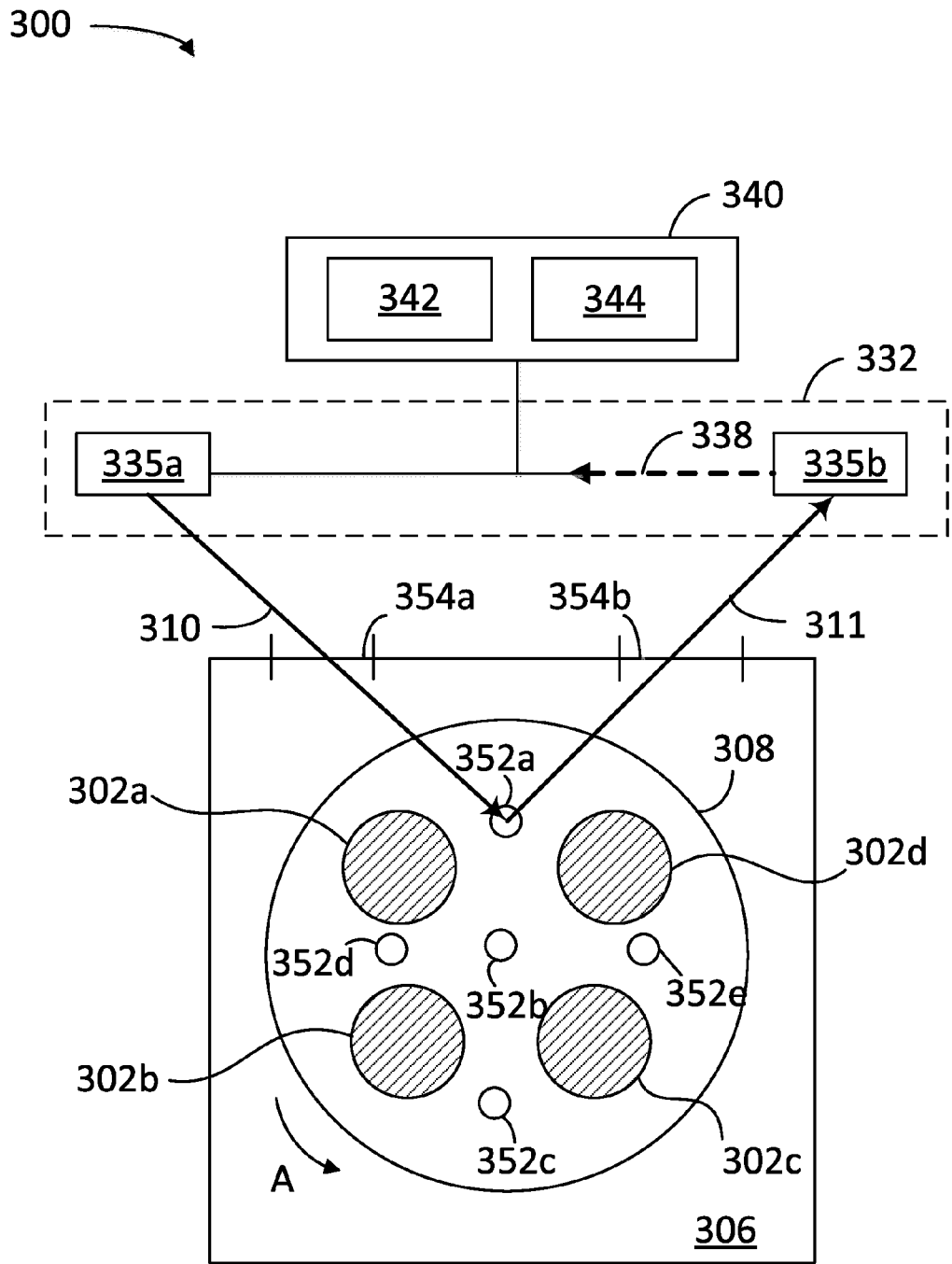
FIG. 3A illustrates a top view of an exemplary system for fabricating a thin-film device, according to some embodiments.

FIG. 3A illustrates a top view of an exemplary system 300 for fabricating a thin-film device, according to some embodiments. System 300 is similar to system 200 (cf. FIG. 2), with the addition of at least one witness sample 352 (shown as witness samples 352a, 352b, 352c, 352d, and 352e) in chamber 306. System 300 also includes a planetary system with a substrate holder 308 that may be configured to move ICEs 302a-302d about an axis at the center of substrate holder 308. Accordingly, one of witness samples 352a-e may be disposed on the center of substrate holder 308, and other witness samples 352a-e may be disposed near ICEs 302a-302d. Similarly to system 200, system 300 includes a measurement device 332 configured to perform optical measurement techniques on at least one witness sample 352a-e. Measurement device 332 may also perform optical measurements on any one of ICEs 302a-d. The optical measurements performed by measurement device 332 may include ellipsometry, spectroscopy, or any other optical technique for measuring a dielectric film thickness.

Measurement device 332 may further include an optical source 335a and a detector 335b. In some embodiments optical source 335a may be a tunable laser capable of emitting or generating electromagnetic radiation 310. In some embodiments, electromagnetic radiation 310 may be polarized, such as used for ellipsometry. In one embodiment, optical source 335a includes an optical parametric oscillator (OPO), or a broadband near-infrared (NIR) and infrared (IR) lamp. Electromagnetic radiation 310 impinges on one witness sample 352a-e and forms reflected electromagnetic radiation 311. Detector 335b may be configured to receive reflected electromagnetic radiation 311 and form a reflection signal 338. Detector 335b may be a thermal detector such as a thermopile or photoacoustic detector, a semiconductor detector, a piezo-electric detector, a charge coupled device (CCD) detector, a video or array detector, a split detector, a photon detector (such as a photomultiplier tube), photodiodes, combinations thereof, or the like, or another detector known to those skilled in the art. Detector 335b may include an optical transducer capable of measurements over a spectral region similar to that capable of being output from optical source 335a. Accordingly, reflection signal 338 may be a voltage, a current, or a combination thereof.

In some embodiments, chamber 306 may contain a first sample window 354a and a second sample window 354b. Chamber 306 may be a fabrication chamber or otherwise a chamber where layers 102, 104 (FIG. 1) of each ICE 302a-d may be progressively built or deposited to predetermined thicknesses. Sampling windows 354a-b may be made from a variety of transparent, rigid or semi-rigid materials that are configured to allow transmission of electromagnetic radiation 310 and reflected electromagnetic radiation 311 therethrough. For example, sampling windows 354a-b may be made of glasses, plastics, semi-conductors, crystalline materials, polycrystalline materials, hot or cold-pressed powders, combinations thereof, or the like.

In at least one embodiment, substrate holder 308 is generally circular and capable of rotation about a central axis, for example, in the direction A. ICEs 302a-d may be radially disposed about substrate holder 308 for rotation therewith. Substrate holder 308 may alternatively be capable of rotation in a direction opposite to direction A. While substrate holder 308 is depicted as containing multiple ICEs 302a-d, it will be appreciated that, in some embodiments, substrate holder 308 may include a single ICE.

In some applications, reflection signal 338 from detector 335b may be conveyed to or otherwise received by a processor 342 communicably coupled to detector 335b. Computational unit 340 has memory 344 including a machine-readable storage medium having instructions stored thereon, which, when executed by a processor 342, causes computational unit 340 to perform a number of operations, such as determining a thickness of a layer deposited on ICEs 302a-d. Accordingly, computational unit 340 may also determine an optical thickness of a layer deposited on ICEs 302a-d by multiplying the physical thickness of the layer times the real part of the index of refraction. The machine-readable storage medium of computational unit 340 may further include one or more stored models or pre-recorded data sets correlating amplitude and phase data of previously measured reflected electromagnetic radiation 311 to a thickness value of the deposited layer. Thus, computational unit 340 may approximate a thickness and a refractive index of layers 102, 104 (FIG. 1) for each ICE 302a-d, as they are formed. Computational unit 340 may be configured to provide a layer thickness in real-time or near real-time, either wired or wirelessly, to an operator for consideration. Thus, a deposition rate is obtained by determining the thickness growth of the layer deposited on at least one ICE 302a-d. Processor 342 in computational unit 340 may determine the deposition rate automatically.

Figure 3B:
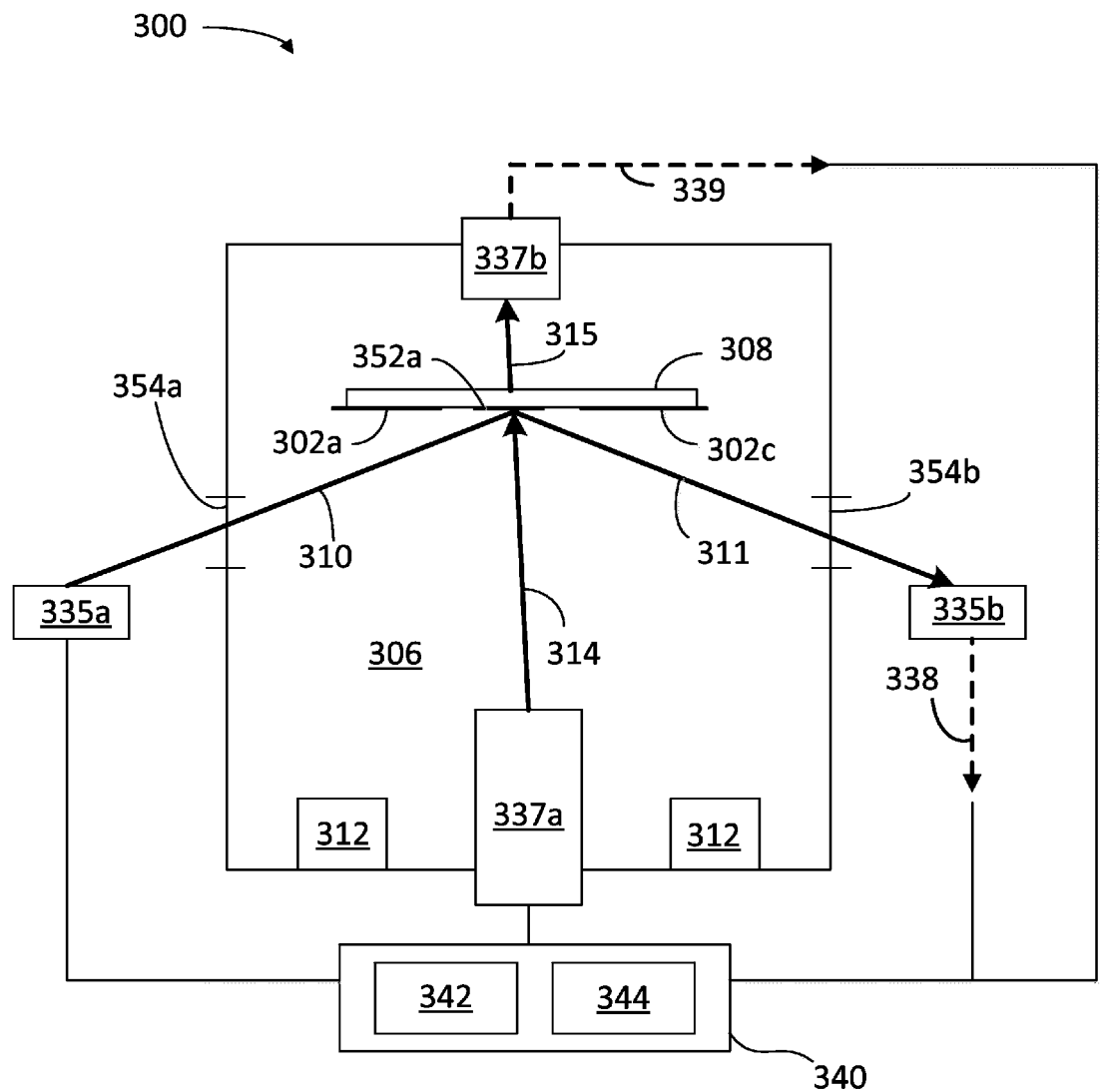
FIG. 3B illustrates a side view of an exemplary system for fabricating a thin-film device, according to some embodiments.

FIG. 3B illustrates a side view of system 300 for fabricating a thin-film device, according to some embodiments. Mass-flux generator 312 may be substantially similar to mass-flux generator 212 of FIG. 2 and therefore will not be described again in detail. Accordingly, in some embodiments mass-flux generator 312 may include an electron gun and a crucible containing a mass source to provide material for depositing a layer on ICEs 302a-d. More generally, mass-flux generator 312 may include any instrument used for deposition of a layer of material on ICEs 302a-d. Optical source 337a may be substantially similar to optical source 335a of FIG. 3A and therefore will not be described again. In that regard, optical sources 335a and 337a may be the same optical source configured to provide electromagnetic radiation 310 and 314, respectively. For example, a beam splitter or a wavelength division multiplexer may separate electromagnetic radiation 310 from electromagnetic radiation 314, both coming from the same optical source. Electromagnetic radiation 314 may have the same optical characteristics as electromagnetic radiation 310 (e.g., polarization, spectral profile, temporal profile, intensity, and modulation). Electromagnetic radiation 314 impinges on witness sample 352a and generates a transmitted electromagnetic radiation 315.

A detector 337b may be disposed in chamber 306 such that it receives transmitted electromagnetic radiation 315. Detector 337b may be configured to receive transmitted electromagnetic radiation 315 and form a transmission signal 339. Detector 337b may be similar in some respects to detector 335b. Accordingly, detector 337b may be a thermal detector such as a thermopile or photoacoustic detector, a semiconductor detector, a piezo-electric detector, a charge coupled device (CCD) detector, a video or array detector, a split detector, a photon detector (such as a photomultiplier tube), photodiodes, combinations thereof, or the like, or another detector known to those skilled in the art. Detector 337b may include an optical transducer capable of measurements over a spectral region similar to that capable of being output from optical source 337a. Accordingly, transmission signal 339 may be a voltage, a current, or combination thereof. FIG. 3B illustrates electromagnetic radiation 310 and electromagnetic radiation 314 impinging on witness sample 352a. In some embodiments, electromagnetic radiation 310 and electromagnetic radiation 314 may impinge on any one of ICEs 302a-d as well as in any one of witness samples 352a-e of FIG. 3A.

Figure 3C:
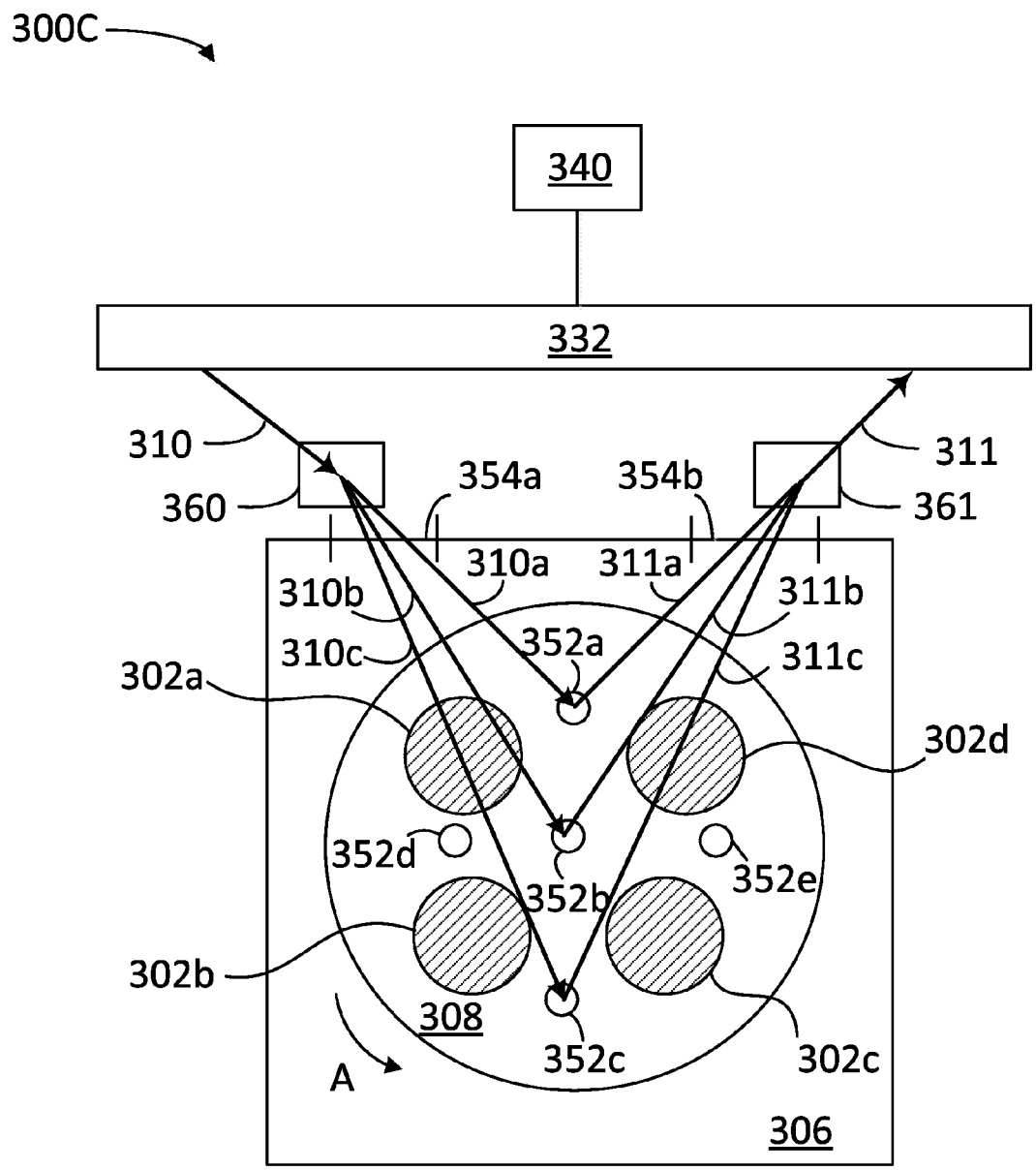
FIG. 3C illustrates a top view of an exemplary system for fabricating a thin-film device, according to some embodiments.

FIG. 3C illustrates a top view of another exemplary system 300C for fabricating a thin-film device, according to some embodiments. System 300C is similar to system 300 of FIGS. 3A-3B and therefore may be best understood with reference thereto, where like numerals will represent like elements not described again. System 300C illustrates an embodiment where electromagnetic radiation 310 is directed to a plurality of witness samples 352a-c. Accordingly, system 300C includes a multiplexing optical device 360 that may be able to separate electromagnetic radiation 310 into multiple beams 310a-c that subsequently impinge on witness samples 352a-c. Likewise, system 300C may include a de-multiplexing optical device 361 that may be configured to collect beams 311a-c reflected from witness samples 352a-c, respectively, to form reflected electromagnetic radiation 311.

Multiplexing optical device 360 and de-multiplexing optical device 361 may include one or more beam splitters, a wavelength division multiplexer (WDM), a time division multiplexer (TDM) or any other splitting optical element separating electromagnetic radiation 310 into multiple beams 310a-c impinging on witness samples 352a-c. In some embodiments, multiplexing optical device 360 and de-multiplexing optical device 361 may include fiber optic components. Further, according to some embodiments, the reflected beams from each of witness sample 352a-c may be directed to a separate detector in measurement device 332. Thickness values may thus be obtained from a plurality of witness samples 352a-c. Measurement device 332 may determine an average deposition rate by weighting/averaging deposition rates obtained from the witness samples 352a-c. Thus, measurement device 332 may provide an accurate deposition rate value to the associated PID loop, according to some embodiments. More specifically, in some embodiments the determined deposition rate is the average of the optical monitor measurements from witness samples 352a-c that are located at about the same distance from the deposition source. Accordingly, in some embodiments a weighted average may correct for different tooling factors between witness samples 352a-c. Such tooling factors may include different relative displacement of a witness samples 352a-c from the deposition source.

Figure 4:
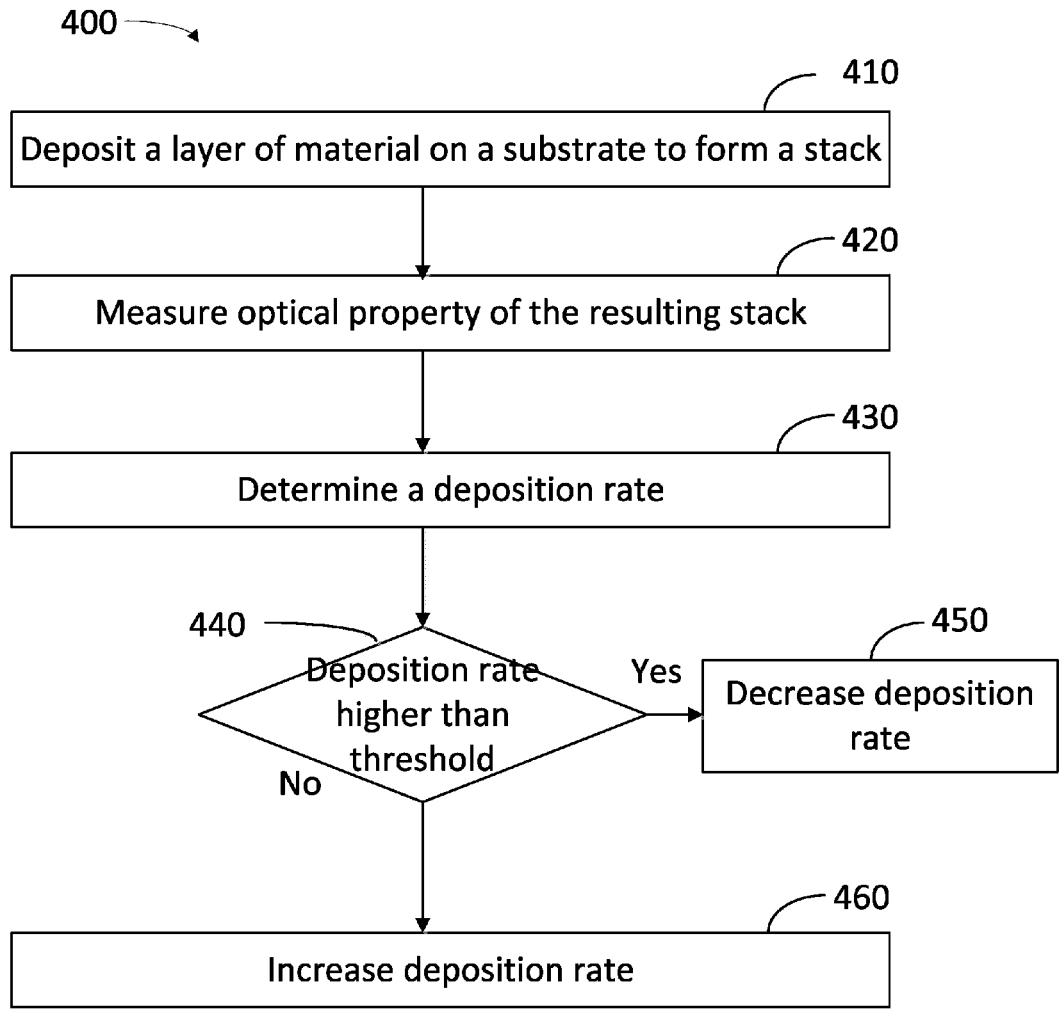
FIG. 4 illustrates a flow chart including steps in a method for controlling a deposition rate for ICE fabrication, according to some embodiments.

FIG. 4 illustrates a flow chart including steps in a method 400 for controlling a deposition rate for ICE fabrication, according to some embodiments. Embodiments of method 400 may include performing the steps illustrated in FIG. 4 in any order or sequence, and not limited to the specific sequence illustrated in FIG. 4. Moreover, embodiments of method 400 consistent with the present disclosure may include employing only one of the steps illustrated in FIG. 4, and not the others. Method 400 may be performed by a system for fabricating an ICE consistent with embodiments disclosed herein (e.g., systems 200, 300, 300C and ICEs 202, 302a-302d, cf. FIGS. 2, and 3A-3C). Accordingly, the system in method 400 may include a measurement device, and at least one witness sample (e.g., measurement devices 232 and 332, and witness samples 352a-d, cf. FIGS. 2 and 3A-3C). Furthermore, the system in method 400 may include a computational unit having processors and memories (e.g., computational units 240 and 340, processors 242 and 342, and memories 244 and 344, cf. FIGS. 2, 3A-3C). At least one memory circuit in the memories may include data and commands which, when executed by the computational unit, cause the processor circuit to perform at least one of the steps in method 400. Moreover, the memory circuit may include an optical model having instructions which, when executed by the computational unit, cause the processor circuit to determine an expected value for an optical measurement, a layer thickness, and a deposition rate.

Step 410 includes depositing a layer of material on a substrate to commence the formation of a stack. Accordingly, step 410 may include performing E-beam deposition, or ion assisted E-beam deposition, or any other material deposition technique as disclosed above (cf. FIG. 2). Moreover, step 410 may include depositing the layer of material on top of at least one layer of material already present in the stack. Further, step 410 may include depositing a first layer of material on a substrate to form the stack (e.g., substrate 204 of FIG. 2). Accordingly, the stack in step 410 may be an ICE, a partially completed ICE, or at least one of a plurality of witness samples. In that regard, step 410 may include depositing the layer of material on a fresh substrate at each step of forming a thin-film stack. More generally, step 410 may include depositing at least a portion of the layer of material. Accordingly, step 410 may include depositing or partially depositing a layer of material of about 1 nm in thickness, or even less.

Step 420 includes measuring an optical property of the resulting stack. Step 420 may also include obtaining a thickness value for the deposited layer using the optical measurement and an optical model. Accordingly, step 420 may include measuring a complex index of refraction of the layer being deposited. Thus, in some embodiments step 420 may include determining an optical thickness of the deposited layer of material. In some embodiments, step 420 may be performed together with depositing the layer of material in step 410. Accordingly, in some embodiments steps 410 and 420 may partially overlap in time, or may be performed simultaneously with each other. More specifically, step 420 may involve measuring an optical property of the resulting stack continuously, during deposition of the material layers in the stack. In that regard, step 420 may include a 'real time' measurement of an optical property of a layer of material as it is being deposited in the stack. In some embodiments, steps 410 and 420 may be performed one after the other, sequentially.

In some embodiments consistent with the present disclosure, step 420 may include performing an ellipsometry measurement on the deposited layer. In some embodiments, step 420 may include performing a spectroscopic measurement on the resulting stack, such as a transmission measurement across a broadband spectral range. In some embodiments, step 420 may include performing a reflectivity measurement across the broadband spectral range. Further, according to some embodiments, step 420 may include performing an interferometry measurement on the deposited layer of material, either in reflection mode, transmission mode, or both.

More specifically, step 420 may include directing an electromagnetic radiation onto the resulting stack using an optical source, and collecting an optically interacted electromagnetic radiation from the resulting stack. Accordingly, the interacted electromagnetic radiation may be collected in transmission mode or in reflection mode. Moreover, step 420 may include splitting the electromagnetic radiation from the optical source into a plurality of optical beams directed to the plurality of witness samples. Step 420 may additionally include collecting a plurality of optically interacted electromagnetic radiations from each of the witness samples. Step 430 includes determining a deposition rate, using the measurement of the thickness of the resulting stack, or the measurement of the thickness of a material layer, as it is being deposited.

Step 440 includes determining whether the deposition rate is higher than a pre-selected threshold. Accordingly, step 440 may include selecting the threshold to achieve consistent optical properties for a plurality of layers of a similar material in the optical thin-film. Step 440 may include determining the deposition rate using the optical property measured in step 420. In some embodiments, the pre-selected threshold may be determined based on a desired stoichiometry for the deposited layer. In some embodiments, the pre-selected threshold may be determined based on the desired material density of the deposited layer. The pre-selected threshold may be determined based on a desired thickness for the layer. For example, in some embodiments step 440 may include reducing the pre-selected threshold when a thickness of the deposited layer approaches a desired thickness value.

Step 450 may include decreasing the deposition rate when step 440 determines that the deposition rate is higher than the threshold. Step 460 may include increasing the deposition rate when step 440 determines that the deposition rate is not higher than the pre-selected threshold. Accordingly, step 460 may include maintaining the deposition rate at the measured level, when the deposition rate is about the same as the pre-selected threshold. In some embodiments, steps 450 and 460 may be performed in the context of a PID loop, in which a correction may include an increase in deposition rate (step 450), or a decrease in deposition rate (step 460).

Accordingly, steps 450 and 460 in a PID loop may include continuously determining a correction amount to the deposition rate based on three contributions. A first contribution is proportional to a difference between a measured deposition rate and the pre-selected threshold. A second contribution is proportional to an integrated value of the difference between the measured deposition rate and the pre-selected threshold. The third contribution may be proportional to a predicted correction to the deposition rate. Accordingly, steps 440 and 450 may include storing the corrected amounts to the deposition rate (decrease, as at step 450, or increase, as at step 460) in the computational unit, to keep historical data. The historical data may be used in method 400 for finding the correction amount, for the deposition rate.

It will be recognized by one of ordinary skill that each of steps 410 through 460 may be performed at least once every time a new layer of material is deposited on the multilayer stack of an ICE. In some embodiments, each of steps 410 through 460 may be performed at least once for every other layer that is deposited on the multilayer stack of the ICE. For example, each of steps 410 through 460 may be performed after a system has deposited a Si layer adjacent to a $SiO_2$ layer in an ICE. In some embodiments, the stack in method 400 may be a single layer formed on a fresh substrate in a new witness sample when performing method 400. This may be the case when step 420 includes measuring a transmission optical property of the witness sample. In such a configuration, it may be desirable to use a single layer on the witness sample, to increase the amount of transmitted electromagnetic radiation through the witness sample. In some embodiments, for example, when step 420 includes measuring a reflection optical property of the witness sample, multiple layers may be accumulated on the witness sample before replacing the witness sample for any further measurement.

It is recognized that the various embodiments herein directed to computer control and artificial neural networks, including various blocks, modules, elements, components, methods, and algorithms, can be implemented using computer hardware, software, combinations thereof, and the like. To illustrate this interchangeability of hardware and software, various illustrative modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the scope of the embodiments expressly described.

Computer hardware used to implement the various illustrative blocks, modules, elements, components, methods, and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable read only memory (EPROM)), registers, hard disks, removable disks, CD-ROMS, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

Embodiments disclosed herein include:

A. A system for fabricating an optical thin-film device that includes a chamber, a material source contained within the chamber, an electrical component to activate the material source, a substrate holder to support a multilayer stack of materials that form the optical thin-film device and at least one witness sample, a measurement device, and a computational unit, wherein the material source provides a layer of material to the multilayer stack and to the witness sample at a deposition rate controlled at least partially by the electrical component and based on a correction value obtained by the computational unit, and wherein the correction value is based on a measured value provided by the measurement device and a computed value provided by the computational unit according to a model.

B. A method for fabricating an optical thin-film device that includes depositing a layer of material on a substrate, measuring an optical property of the layer to obtain a deposition rate, determining a pre-selected threshold based on an optical model, decreasing the deposition rate when the deposition rate is higher than the pre-selected threshold, and increasing the deposition rate when the deposition rate is lower than the pre-selected threshold.

C. A method of forming an optical thin-film device that includes depositing a layer of material on a substrate, measuring an optical property of the layer to obtain a deposition rate, selecting a threshold to achieve consistent optical properties for a plurality of layers of a similar material in the optical thin-film device, decreasing the deposition rate when the optical property is lower than the threshold, and increasing the deposition rate when the optical property is higher than the threshold.

Each of embodiments A, B, and C may have one or more of the following additional elements in any combination: Element 1: wherein the material source includes two materials having a first index of refraction and a second index of refraction, and the multilayer stack comprises at least a first layer formed of the first material and at least a second layer formed of the second material. Element 2: wherein the measurement device comprises an optical measurement device including at least one of an ellipsometer, a spectrometer, and an interferometer. Element 3: wherein the optical measurement device comprises an optical source configured to generate an electromagnetic radiation and a detector configured to measure an interacted electromagnetic radiation. Element 4: wherein the optical measurement device is configured in one of a transmission mode, a reflection mode, and a transmission and reflection mode. Element 5: wherein the optical thin-film device is an integrated computational element used for analyzing a substance in real time.

Element 6: wherein measuring the optical property of the layer comprises continuously measuring the optical property as the layer is being deposited. Element 7: wherein measuring the optical property of the layer comprises measuring an interacted electromagnetic radiation transmitted through at least a portion of the layer. Element 8: wherein measuring the optical property of the layer comprises measuring an interacted electromagnetic radiation reflected from at least a portion of the layer. Element 9: wherein decreasing the deposition rate comprises determining that an optical thickness of the layer of material is less than a desired optical thickness. Element 10: wherein decreasing the deposition rate comprises determining that a material density of the layer of material is lower than a desired material density. Element 11: wherein increasing the deposition rate comprises determining that a material density of the layer of material is higher than a desired material density. Element 12: wherein the pre-selected threshold is based on a stoichiometry of the layer of material. Element 13: wherein the pre-selected threshold is based on a desired index of refraction of the layer of material. Element 14: wherein measuring an optical property comprises performing at least one of an ellipsometer measurement, a spectrometer measurement, an interferometer measurement, and a continuous multi-wavelength measurement. Element 15: wherein determining the pre-selected threshold comprises performing a PID loop including the optical model, the measured deposition rate, and at least a previously measured deposition rate.

Element 16: wherein measuring the optical property of the layer comprises continuously measuring the optical property as the layer is being deposited. Element 17: wherein the threshold is a desired material density of the layer of material. Element 18: wherein measuring the optical property comprises measuring an optical density. Element 19: wherein the threshold is based on a desired stoichiometry of the layer of material. Element 20: wherein the threshold is based on a desired optical thickness of the layer of material.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners, apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:

1. A system for fabricating an optical thin-film device, comprising:
    a chamber;
    a material source contained within the chamber;
    an electrical component to activate the material source;
    a substrate holder arranged within the chamber to support a plurality of witness samples and a multilayer stack of materials that form the optical thin-film device;
    a measurement device having an optical source and a detector each in optical communication with the plurality of witness samples, the measurement device being operable to measure and provide an optical property from the plurality of witness samples; and
    a computational unit communicably coupled to the electrical component and the measurement device, wherein deposition of the material source by the electrical component provides a layer of material to the multilayer stack of materials and to the plurality of witness samples at a deposition rate controlled based on a correction value obtained by the computational unit, and
    wherein the correction value is based on a weighted average of the optical property from the plurality of witness samples and a computed value provided by the computational unit according to an optical model, the weighted average based on a difference between a plurality of tooling factors associated with a location of each of the plurality of witness samples.

2. The system of claim 1, wherein the material source includes two materials having a first index of refraction and a second index of refraction, and the multilayer stack of materials comprises a first layer formed of a first material and at least a second layer formed of a second material.

3. The system of claim 1, wherein the measurement device comprises an optical measurement device including at least one of an ellipsometer, a spectrometer, and an interferometer.

4. The system of claim 3, wherein the optical source generates an electromagnetic radiation and the detector measures an interacted electromagnetic radiation.

5. The system of claim 3, wherein the optical measurement device is configured in one of a transmission mode, a reflection mode, and a transmission and reflection mode.

6. The system of claim 1, wherein the optical thin-film device is an integrated computational element used for analyzing a substance in real time.

7. A method for fabricating an optical thin-film device, the method comprising:
    depositing a layer of material on a plurality of substrates associated with a plurality of witness samples, each witness sample located in a different location;
    measuring an optical property of the layer of material to obtain a deposition rate for each of the plurality of witness samples;
    determining a pre-selected threshold based on a weighted average of the optical properties of the plurality of witness samples in an optical model, the weighted average determined according to a difference between a plurality of tooling factors associated with the different location of the plurality of witness samples;
    decreasing the deposition rate when the deposition rate is higher than the pre-selected threshold; and
    increasing the deposition rate when the deposition rate is lower than the pre-selected threshold.

8. The method of claim 7, wherein measuring the optical property of the layer of material comprises continuously measuring the optical property as the layer of material is being deposited.

9. The method of claim 7, wherein measuring the optical property of the layer of material comprises measuring an interacted electromagnetic radiation transmitted through at least a portion of the layer of material.

10. The method of claim 7, wherein measuring the optical property of the layer of material comprises measuring an interacted electromagnetic radiation reflected from at least a portion of the layer of material.

11. The method of claim 7, wherein decreasing the deposition rate comprises determining that an optical thickness of the layer of material is less than a desired optical thickness.

12. The method of claim 7, wherein decreasing the deposition rate comprises determining that a material density of the layer of material is lower than a desired material density.

13. The method of claim 7, wherein increasing the deposition rate comprises determining that a material density of the layer of material is higher than a desired material density.

14. The method of claim 7, wherein the pre-selected threshold is based on a stoichiometry of the layer of material.

15. The method of claim 7, wherein the pre-selected threshold is based on a desired index of refraction of the layer of material.

16. The method of claim 7, wherein measuring an optical property comprises performing at least one of an ellipsometer measurement, a spectrometer measurement, an interferometer measurement, and a continuous multi-wavelength measurement.

17. The method of claim 7, wherein determining the pre-selected threshold comprises performing a proportional-integral-derivative (PID) loop including the optical model, the deposition rate, and at least a previously measured deposition rate.

18. A method of forming an optical thin-film device, comprising:
    depositing a layer of material on a plurality of substrates associated with a plurality of witness samples, each witness sample located in a different location;
    measuring an optical property of the layer of material to obtain a deposition rate for each of the plurality of witness samples;
    selecting a threshold to achieve a weighted average of the optical properties of the plurality of witness samples, the weighted average determined according to a difference between a plurality of tooling factors associated with the different location of the plurality of witness samples, and according to an optical model for a plurality of layers of a similar material in the optical thin-film device;
    decreasing the deposition rate when the optical property is lower than the threshold; and
    increasing the deposition rate when the optical property is higher than the threshold.

19. The method of claim 18, wherein measuring the optical property of the layer comprises continuously measuring the optical property as the layer is being deposited.

20. The method of claim 18, wherein the threshold is a desired material density of the layer of material.

21. The method of claim 18, wherein measuring the optical property comprises measuring an optical density.

22. The method of claim 18, wherein the threshold is based on a desired stoichiometry of the layer of material.

23. The method of claim 18, wherein the threshold is based on a desired optical thickness of the layer of material.

* * * * *